United States Patent [19]

Bignami et al.

[11] Patent Number: 5,118,607
[45] Date of Patent: Jun. 2, 1992

[54] NON-AQUEOUS SOLVENT SPECIFIC BINDING PROTEIN ASSAYS

[75] Inventors: Gary S. Bignami, Waialua; Paul G. Grothaus, Mililani, both of Hi.

[73] Assignee: Hawaii Biotechnology Group, Inc., Aiea, Hi.

[21] Appl. No.: 606,875

[22] Filed: Oct. 31, 1990

Related U.S. Application Data

[63] Continuation-in-part of Ser. No. 425,759, Oct. 23, 1989, abandoned.

[51] Int. Cl.⁵ .................. C12Q 1/00; G01N 33/53; G01N 33/566; G01N 33/543
[52] U.S. Cl. .................. 435/7.1; 435/7.95; 435/7.94; 435/7.93; 435/7.92; 436/501; 436/518; 436/527
[58] Field of Search .......... 435/4, 7, 7.92, 7.95, 435/7.93-7.94, 7.1; 436/501, 513, 828, 824, 811, 518, 524, 501, 518, 527

[56] References Cited

U.S. PATENT DOCUMENTS 4,115,538 9/1978 Satoh et al. .................. 424/1

OTHER PUBLICATIONS

The Merck Index (1983), pp. 1073, 970, The Merck & Co, Rahway N.J.
Tinoco et al. Physical Chemistrty, Prentice-Hall, N.J., 1987, pp. 85-90.
Kabanov et al., A New Way in Homogeneous Immunoassay: Reversed Micellar Systems as a Medium for Analysis, Analyt. Biochem 181:145-8, 1989.
Zaks et al. Enzyme Catalysis in Non-Aqueous Sovents. J. Biol. Chem 263(7):3194-3201 Mar. 1988.
Russell et al. Antibody-Antigen Binding in Organic Solvents. Biochem Biophys Res Com 158(1) 80-5 Jan. 89.

*Primary Examiner*—Christine Nucker
*Assistant Examiner*—David P. Preston
*Attorney, Agent, or Firm*—Barbara Rae-Venter

[57] ABSTRACT

Novel specific protein binding assays are provided employing a solvent system comprising a solvent characterized as hydrophobic, essentially anhydrous and water immiscible. Particularly, lipophilic analytes are shown to be sensitively determined using antibodies in hydrocarbon media, optionally substantially saturated with aqueous buffer and/or comprising an anionic surfactant.

22 Claims, No Drawings

NON-AQUEOUS SOLVENT SPECIFIC BINDING PROTEIN ASSAYS

CROSS-REFERENCE TO RELATED APPLICATIONS

This application is a continuation-in-part of USSN 07/425,759 filed Oct. 23, 1989, abandoned which disclosure is hereby incorporated by reference.

INTRODUCTION

1. Technical Field

The field of this invention is the determination of the presence of an analyte involving the presence of a specific binding protein, particularly in water-immiscible solvents.

2. Background

The use of specific receptors or the detection of such receptors has found extensive exploitation, particularly in the medical field. In the medical field, one has been interested in a wide variety of drugs and naturally occurring compounds and physiological fluids. These compounds are for the most part water soluble at the concentrations of interest. The assays are frequently based on the specific recognition by a protein of a proteinaceous or non-proteinaceous analyte, where the binding of the protein receptor and its complementary ligand normally occurs in an aqueous medium.

In many situations, there may be an interest in using a non-aqueous medium. In some situations, one wishes to extract a hydrophobic compound from a specimen such as soil, fat, or the like, where it would be desirable to retain the extracted compound in a non-aqueous medium. In chemical processing, where organic solvents are employed, there will be many situations where one wishes to monitor the presence of minor impurities in the reaction mixture. The need to transfer the sample into an aqueous medium may preclude any measurement.

There is, therefore, substantial interest in being able to develop assays which provide for specific recognition of analytes while allowing for the use of non-aqueous solvents.

3. Relevant Literature

Durfor et al., *J.A.C.S.* (1988), 110:8714–8716, describe antibody catalysis in reverse micelles. Zaks and Klibanov, *J. Biol. Chem.* (1988), 263:3194–3201, describe enzymatic catalysis in non-aqueous solvents. See also Chemical and Engineering News, Jul. 2, 1984, page 23. Zaks and Klibanov, *Science* (1984), 224:1229–1231, describe enzymatic catalysis in organic media at 100° C. Russell and Klibanov, *J. Biol. Chem.* (1988), 263:11624–11626, describe inhibitor-induced enzyme activation in organic solvents. Kazandjian et al., *Biotechnology and Bioengineering* (1986), 23:417–421, describe enzymatic analyses in organic solvents. Kazandjian and Klibanov, *J.A.C.S.* (1985), 107:5448–5450, describe regioselective oxidation of phenols catalyzed by polyphenol oxidase in chloroform. Klibanov, Enzymes That Work In Organic Solvents, *Chemtech* (Jun. 1986), 354–359, discusses enzymatic catalysis in organic solvents. Zaks and Klibanov, *J.A.C.S.* (1986) 108:2767–2768, compare substrate specificity of enzymes in organic solvents in relation to water. Klibanov, *TIBS* (1989) 14:141–144, describes enzymatic catalysis in anhydrous organic solvents. Russell et al., *Biochem. and Biophys. Res. Comm.* (1989), 158:80–85, describe antibody-antigen binding in hydrophilic organic solvents.

SUMMARY OF THE INVENTION

Specific binding protein assays are provided for detecting the presence of a lipophilic analyte in a sample using a solvent system comprising an essentially anhydrous, hydrophobic, water immiscible solvent. The process employs a proteinaceous receptor wherein the lipophilic analyte and the receptor are members of a specific binding pair which bind to form a complex. The method comprises the steps of combining the sample, the solvent system and a reagent system for providing a detectable signal, together with any additional reagents for detecting complex formation between the analyte and the receptor, and detecting the presence of the signal, where a decrease in the amount of signal detected in the sample as compared to a control containing no analyte is indicative of the presence of said analyte. Optionally, a small amount of aqueous buffer and/or surfactant may be added to the solvent system.

DESCRIPTION OF SPECIFIC EMBODIMENTS

Novel specific binding protein assays are provided employing a solvent system comprising an essentially anhydrous water immiscible organic solvent, particularly hydrocarbons or halohydrocarbon, as the assay medium. The sample, containing an analyte which is one member of a specific binding pair may be pretreated as desired, and dispersed in the assay medium. The assay medium may then be combined with the complementary member of the specific binding pair, generally a proteinaceous receptor, and the mixture allowed to incubate for reaction to occur between the specific binding protein and its complementary ligand. For heterogenous assays, the assay medium may be separated from the solid support, the solid support washed and the distribution of the label determined by determining the amount of label bound to the support or the amount of label in the supernatant, optionally combined with the washes. A decrease in the amount of bound label detected in the test sample as compared to a control sample containing no ligand is indicative of the presence of ligand in the test sample.

The use of hydrophobic solvents offers the advantage that ligands not readily assayed in aqueous media may be readily assayed. The solvent system may optionally contain a small amount of aqueous buffer and/or a surfactant. The addition of surfactant to the solvent system offers the advantage that the amount of non-specific binding, or signal to noise ratio, generally is lower when surfactant is used. The omission of surfactant offers the advantage of a more direct method, and finds particular use in an automated system using for example a biosensor system which automatically blanks out the non-specific binding.

The sample may be any industrial or biological material in which an analyte is present, particularly where the analyte is a hydrophobic compound. Biological samples may be animal or plant tissue, physiological fluid, feces, bile, fat or plasma samples. Industrial samples may include soil samples and industrial organic chemicals whether they be final products, process intermediates or wastes from the pharmaceutical, pesticide and like industries. In many plant and animal tissues, the presence of various organic compounds may be of interest. For example, detection of aflatoxin in peanuts, pesticides in animal fat, or the like may be of interest. In soils, particularly soils associated with industry, such as chemical processing, synthesis of organic compounds, particularly pesticides, the electronic industry, or the like, various organic compounds may seep into the soil. The determination of the presence of these compounds can be important in determining whether waste storage is leaking, whether there has been violation of rules and regulations concerning disposal of compounds, presence of hazardous materials in chemical waste drums, Quality Control of bulk organic chemicals and process intermediates, or the like. In addition, there are a number of lipid soluble compounds in physiological fluids or tissues which are of interest. These include endogenous compounds, toxic compounds, therapeutics and illicit drugs.

With many of these samples, it may be necessary or desirable to extract lipid soluble material into an organic solvent. Thus, the extract will provide the sample to be used. For extraction, the same solvent as used as the assay medium is not required, so long as the extracting solvent is substantially miscible with the assay medium in the amounts used. Thus, various solvents may be used, which have higher hydrophilicity than the solvents used in the subject assays. In some instances, the compound of interest may be dispersed in an aqueous medium due to the presence of solubilizing compounds such as proteins or detergents. In this instance, so long as the sample is small and can be dispersed in the hydrophobic assay medium without separation, the sample may be used directly.

In carrying out the assay, the sample suspected of containing the analyte will be combined with the assay medium. The assay medium has a major portion an organic solvent, a liquid at the temperature of the assay, preferably combined with not more than about 2%, usually not more than about 0.2%, by volume of an aqueous buffer and up to about 5 mM of a surfactant, e.g., an anionic, non-ionic or cationic, particularly anionic. Larger amounts of water, up to 5% (w/w) may be used. The surfactant while not essential for obtaining specific binding as compared to non-specific binding is particularly desirable.

The organic solvent is characterized as being hydrophobic, essentially anhydrous, and water immiscible. By hydrophobic is intended that the solvent will usually dissolve less than 7.0% (w/w) more usually less than 5% (w/w) of water. By essentially anhydrous is intended anhydrous grade solvents which depending upon the solvent, generally contain <0.1% (w/w) water, more usually <0.05% (w/w) water and may contain <0.005% (w/w) water. By water immiscible is intended solvents that cannot be uniformly mixed or blended with water, i.e. two phases are formed upon mixing with water. For the most part, the solvents will be hydrocarbons or halohydrocarbons, aliphatic, aromatic and alicyclic, where the halohydrocarbons have halogen of atomic numbers 9 or 17, although 0-2 heteroatoms, e.g., O, N or S, may be present where the carbon/heteroatom ratio is at least about 4:1. Desirably the solvents are aliphatic hydrocarbons of from 5 to 18 carbon atoms, particularly of from 6 to 16 carbon atoms, particularly straight chain. The halohydrocarbons will generally be of from about 1 to 6 carbon atoms, more usually from 1 to 4 carbon atoms, generally containing at least one halogen and up to perhalo. Illustrative solvents include hexane, heptane, octane, decane, dodecane, pentadecane, hexadecane, 2,6-dimethyloctane, toluene, benzene, the xylenes, cumene, cyclooctane, chloroform, dichloromethane, carbon tetrachloride, etc. The solvents may also contain heterogroups such as nitro, for example nitrobenzene and heteroatoms such as halogens so long as the characteristics of the solvent are maintained.

The assay medium will normally contain not more than about 5% (w/w), usually not more than about 2%, preferably not more than about 0.2% by volume of a buffer solution, at a pH from about 5 to 10, more usually 6 to 9. For the most part, the solvents which dissolve less than about 0.2% (w/w) of the buffer medium will be saturated with the buffer medium, i.e. the buffer will be present at the solubility limit. Generally, the buffer will be present in from about 10 to 200 mM, usually 50 to 150 mM, and various buffers may be used, such as phosphate, phosphate buffered saline, carbonate, Tris, MOPS, HEPES, or the like. Of particular interest, are inorganic buffers. Salts may be present, e.g., NaCl, other than the buffer, generally ranging in an amount from about 0 to 1.0% (w/v).

The third ingredient of the medium may be a surfactant, particularly an anionic surfactant, which may be aromatic or aliphatic, particularly aliphatic, normally a salt of an organic acid or ester, including carboxylates, sulfonates, sulfates, phosphonates, cationic surfactants include CTAB, while nonionic surfactants include polyoxyethylene glycol ethers and esters, or combinations thereof. Other functionalities may be present in the surfactant, particularly oxygen containing functionalities, such as ethers, esters, carbonyls, hydroxyl, or the like. Of particular interest is the diester of sulfosuccinate where the alkyl groups may be of 6 to 12 carbon atoms, particularly 8 carbon atoms. The concentration of the surfactant will vary depending upon the particular surfactant, generally not exceeding about 5 mM, preferably being from about 0.02 to 3 mM, more preferably from about 0.1 to 2 mM. The surfactant may be added to the solvent either in the presence or absence of buffer, preferably in the presence of buffer. The surfactant may serve to minimize non-specific binding.

The dilution of the sample into the assay medium will depend upon the concentration of the analyte in the sample, the nature of the medium containing the sample, and the like. Usually, the sample will be less than about 50 volume % of the assay medium, usually less than about 20 volume % of the assay medium and may be as small as 1% or less of the assay medium.

In carrying out the subject invention, various assay protocols may be used, particularly heterogeneous protocols. By heterogeneous is intended that bound and free are separated. At least one of the components of the assay system may be bound to a solid support. Generally, the component bound is one member of a specific binding pair ("receptor") capable of binding specifically to an analyte or ligand (second member of the specific binding pair). The receptor generally will be proteinaceous, and will usually be an antibody or fragment thereof, including the various isotypes, e.g., murine IgG1, IgG2a, IgG2b, IgG3, IgM, IgA, IgD and IgE, fragments such as F(ab)2, Fab,, Fv, etc. Following combination of the sample with the assay medium as described above, the solvent medium may then be combined with the immobilized receptor and the mixture allowed to incubate for reaction to occur between the receptor and the ligand. For heterogeneous assays, the solvent medium may be separated from the solid support, the solid support washed and the distribution of a label obtained by determining the amount of label bound to the support or the amount of label in the supernatant, optionally combined with the washes.

The protocols involve a reagent system comprising a labelled compound which provides for detection of complex formation between the ligand and the receptor. The term label is intended to mean any compound which allows, either directly or indirectly, the detection of the presence of a member of a specific binding pair, particularly as to the presence or absence of complex formation between the ligand and its receptor. Various labels which find use include radioisotopes, fluorescers, chemiluminescers, enzymes, including PEG-modified enzymes, beads, including beads containing a chromophore, graphite, metallic beads, etc. The label need not be directly bound to the member of the specific binding pair forming the complex, but rather may be bound indirectly, such as using a second specific binding pair. For example, biotin may be present as the label on the first specific binding pair, which may then be bound to avidin or streptavidin, which is labelled with a label capable of providing a detectable signal. Fluorescers include fluorescein, rhodamine, umbelliferone, BBD (7-benzylamino-4-nitrobenzoxadiazole), and the like. Radioisotopes include 14C, 32P, 125I, 3H, and the like. For the most part, the labels are well known and do not require further exemplification here.

The reagent system will be comprised of the labeled conjugate and such other reagents as are necessary for detection of the label. For enzymes, this will usually include substrates. For chemiluminescers, other reactants may be required to produce the chemiluminescence. In other situations, the reagent system may involve antibodies to fluorescers, quencher conjugated antifluorescer, and the like. The components of the reagent system may be combined concurrently or consecutively, depending on the nature of the reagent system.

For heterogeneous assays, the receptor will normally be bound to a solid support. Solid supports may include rods, beads, membranes, vessels, for example, microtiter wells, or the like. Various materials may be involved, such as glass, nylon, Mylar, controlled pore glass, or other support which will not be adversely affected by the assay medium. Immobilization of the receptor may be achieved in a variety of conventional ways, usually employing covalent binding in accordance with conventional techniques. The glass products can be readily activated by heating the glass at elevated temperature, generally in the range of about 400 to 600° C. After cooling the glass is functionalized by reaction with an appropriately functionalized silane. Controlled pore glass needs no activation prior to silane functionalization. Thus, halodialkoxy or trialkoxycarboxyalkyl or -aminoalkyl silanes may be employed. Functionalized supports may be readily conjugated to the receptor using various reagents, such as glutaraldehyde, maleimidobenzoic acid, where the protein has a mercapto group, or where sugars are present on the protein, these may be oxidized to dialdehydes for linkage under reducing conditions to an amine, to form a methyleneamine or imine. After reaction of the specific binding protein to the surface, the surface may then be washed with an aqueous medium, particularly one containing inert γ-globulin. After incubation with γ-globulin containing solution, the surface may then be exhaustively washed with an aqueous medium, particularly phosphate buffered saline.

The particular order of addition will vary depending upon the nature of the protocol. In heterogeneous assays, usually the sample containing the ligand analyte and the receptor will be combined either concurrently with the labelled ligand analog or prior to the addition of the labelled ligand analog. For homogenous assays, a similar order of addition may be employed, although one may be preferred over the other. Depending upon the nature of the assay, either a rate or equilibrium determination may be made, using one or more determinations. Generally, the time for the determination will be at least about 30 sec and may be 24 hr or more, usually at least about 2 min and not more than about 12 hr. Rate determinations will vary, generally beginning at least about 1 min after combining with the labelled ligand analog and usually requiring at least 1 min between readings, more usually at least about 2 min and not more than about 6 hr.

The temperature for the reaction may vary from about −20 to 40° C., more usually from about 0 to 22° C. For the most part, the receptors will be naturally occurring receptors or antibodies, particularly monoclonal antibodies, although antisera may find application. Various naturally occurring receptors include thyroxine binding protein, lipoproteins, surface membrane proteins, etc.

The analytes of interest may be varied widely, including pesticides, such as insecticides, herbicides, nematocides, fungicides, pollutants, toxins, such as aflatoxin, physiologically active compounds, and such other compounds as may be hydrophobic and of interest. For the most part, the ligands will be haptenic and less than about 5 kD, usually less than about 2 kD.

Depending upon the nature of the label, various techniques may be employed for detection of the signal. Equipment is generally available, such as scintillation counters for radioisotopes, spectrophotometers for dyes, fluorimeters for fluorescence and chemiluminescence, and the like.

The following examples are offered by way of illustration and not by way of limitation.

EXPERIMENTAL

Abbreviations

PBS-T = PBS + 0.05% (v/v) Tween-20
NRIgG = normal rabbit IgG
BSA = Bovine serum albumin
PBS = 0.01 M Sodium phosphate, 0.15 M NaCl (pH 7.0)
PBS/BSA = PBS + 1% BSA
OPP = Octane containing 1 M 1-propanol and 0.1% PBS (v/v)
CPG = Controlled pore glass

Materials

Antigen specific sera were purchased from the suppliers listed in Table 1. They were stored at 4° C. until use.
Purified normal rabbit IgG (Pierce)
Protein G columns (Genex, GammaBind ™ -G)
Rabbit IgG standards (Sigma)
[$^3$H]Estradiol (Amersham), 94 Ci/mmol
[$^3$H]Progesterone (Amersham), 85 Ci/mmol
[$^3$H]Digitoxin (New England Nuclear), 15.8 Ci/mmol
Ecolume liquid scintillation cocktail (ICN)

CPG glass beads, 20 mesh, pore dia 1273, pore dist
  ±8.4%, CPG Inc. Fairfield NJ lot #100CC
  09DO1
Nylon 6/6 rods (Aldrich Chemical Co.), 3×2 mm
Pyrex TM rods—5x3 mm
Pyrex TM beads—(Baxter) 3 mm dia.
Karl Fischer reagent—(Fisher Scientific)
Solvents—(Aldrich Chemical Co.), anhydrous grade
AOT (Sigma)—dioctyl sulfosuccinate sodium salt 1. Antibody Preparation and Quality Control a. Preparation of purified rabbit IgG fractions from whole sera Protein G chromatography was used to isolate the IgG fraction of rabbit sera. Protein G columns containing 1.0 ml recombinant protein G covalently immobilized on Sepharose=4B were used to isolate the IgG fraction from rabbit sera. Protein G chromatography was performed as follows: Serum samples were clarified by centrifugation for 15 min (16,000 ⋅ g) and diluted 1:1 in PBS loading buffer. Protein G columns were equilibrated with 10 ml PBS and one milliliter of diluted serum was then loaded onto the column. Unbound protein was washed from the column with PBS at a flow rate of 1 ml/min. using a peristaltic pump. Eluted protein was monitored by UV absorbance at 280 nm. When A280 had returned to baseline values, bound IgG was eluted with 2 ml of 0.5 M ammonium acetate (pH 3.0). IgG fractions were collected into tubes containing equal volumes of 1.5 M Tris-HCl (pH 8.8) in order to allow rapid neutralization of the elution buffer pH. Fractions containing IgG were combined and dialyzed extensively against PBS. Immunoglobulin concentration was estimated by UV spectroscopy at 278 nm using an extinction coefficient of 1.4 mg/ml.

Purity of rabbit IgG fractions was assessed by SDS-PAGE (Laemmli, Nature (1970), 277:680) and visualized by the silver staining method (Hukeshoven and Dernick Electrophoresis (1985), 6:103). Protein G chromatography resulted in purification estimated to be ≥90% when compared to rabbit IgG standards.

Protein G purified IgG fractions were checked for antigen binding capacity by a precipitation RIA, as described below. Binding capacity of the IgG fractions was retained following chromatography.

b. Precipitation RIA method:

0.36 ml of antibody preparation serially diluted in PBS +1% BSA and 0.04 ml radiolabelled antigen (0.1μCi) were combined and mixed, then incubated for 1 hr at 37° C. in a water bath. Then 0.1 ml of a 0.1M EDTA, (ethylenediamine tetraacetic acid) in water solution pH 7.0 and 0.2 ml of a 2% (v/v) normal rabbit serum in PBS +1% BSA solution were added to each sample and mixed. Then 0.1 ml of an optimally diluted goat anti-rabbit IgG and 0.5 ml of a 6% (w/v) polyethylene glycol 6000 in PBS +1% BSA solution was added to each sample, mixed, and incubated for 5 min at ambient room temperature. Each sample was then centrifuged at 15,000×g for 15 min at 4° C. The pelleted material was washed by centrifugation 3 times with 0.5 ml PBS +1% BSA and the precipitate solubilized with 0.3 ml of 0.1N NaOH. 0.15 ml of the dissolved pellet was then added to 3 ml scintillation cocktail and the radioactivity quantified using standard liquid scintillation counting techniques.

c. Immobilization

Four different types of support materials were evaluated for the immobilization of the antibodies: Controlled pore glass (CPG) beads, nylon rods, and activated Pyrex TM glass rods and Pyrex glass beads. The CPG and Pyrex TM beads (or rods) were cleaned by treatment with 5% nitric acid at 100° C. for 1 hr followed by extensive rinsing with distilled water and acetone. The glass surface of the Pyrex beads and rods was activated by heating at 500° C. for 5 hr followed by cooling to room temperature in a desiccator (Hamaguchi et al., J. Biochem. (1976), 80:895-898). No activation was necessary for the CPG beads. The beads (or rods) were then immersed in a 2% solution of 3-aminopropyl-triethoxysilane in acetone and allowed to stand at 45° C. for 24 hr. After cooling to room temperature, the aminated glass beads (or rods) were washed repeatedly with acetone and stored in a desiccator until used. Nylon 6/6 rods were activated by incubation in 3.5 M HCl for 24 hr (Hendry and Herman J. Immunol. Methods (1980), 35:285-296). The nylon rods were then washed with distilled water, washed for 1 min in 0.1 M carbonate buffer (pH 9.5), washed with PBS and stored in a desiccator at 0° C. until needed.

Antibodies were immobilized on the supports using Robinson's modification (Robinson et al., Biochem. Biophys. ACTA, (1971), 242:659-661) of the general method of Weetall (Meth. Enzymol. (1976), 44:134-147). Thirty-six aminated Pyrex TM beads (or rods), 36 nylon rods or 500 mg of aminated CPG beads were treated with 8% aqueous glutaraldehyde for 30 min at room temperature. The beads (or rods) were thoroughly washed with distilled water and suspended in 2 ml of PBS containing 720 μg of purified IgG and allowed to stand at 4° C. for 24 hr: The beads were then washed with PBS and resuspended in 2 ml of PBS containing 720 μg of normal rabbit IgG. After standing at room temperature for 2 hr, the beads were exhaustively washed with PBS. The liquid was decanted off and the beads were frozen and lyophilized.

Experiments to determine the optimal solid phase were conducted in parallel with organic phase antigen-binding assays. Initial assays employed IgG immobilized on CPG. However, the use of CPG beads in preliminary experiments proved to be technically cumbersome. Not only did each sample require accurate weighing, but full recovery of the beads following sample washing was difficult. In an effort to find a more reliable solid phase support, nylon rods and Pyrex glass rods were evaluated. The Pyrex TM rods proved to be most suitable, however, there was too great a variation in size of the available rods. The Pyrex TM beads were readily available in quantity and proved to be just as suitable as the Pyrex TM rods. While the size distribution of these beads was not as narrow as preferred, they were more uniform than the rods. Since size variations of the beads could increase the variability of the assays, we sorted the beads as much as possible.

d. Storage

Immobilized antibodies were stored in a vacuum desiccator over Drierite TM at 4° C. until use. They were allowed to equilibrate to room temperature before the vacuum was released.

2 Solvents a. Purity

Organic solvents were anhydrous grade, certified to contain <0.005% H2O. The water content of the solvents was checked by Karl Fischer titratio and found to be below the level of detection.

EXAMPLE 1

Solid Phase Antigen-binding Assays

Determination of the immobilized antibody binding activity by aqueous RIA

Controlled pore glass (CPG): Five milligrams of beads with immobilized anti-estradiol (lot #554-C) or immobilized BSA were added to duplicate 1.5 ml Eppendorf tubes. Beads were incubated in 0.4 ml PBS/BSA containing 0.1 µCi [$^3$H]estradiol for 1 hr at room temperature, with shaking at 200 rpm. Following incubation, samples were washed three times by centrifugation with 1.5 ml PBS/BSA. Beads were transferred to scintillation vials and bound radioactivity was determined by liquid scintillation counting in 3 ml Ecolume cocktail. Antiestradiol (lot #554-C) immobilized on controlled pore glass beads was shown to bind approximately 2500 cpm vs 500 cpm for the immobilized BSA background.

Glass and nylon rods: One glass or nylon rod with immobilized anti-estradiol or immobilized BSA was added to duplicate 7 ml glass scintillation vials. Samples were incubated in 0.4 ml PBS/BSA containing 0.1 µCi [$^3$H]estradiol for 1 hr at room temperature, without agitation. Rods were washed three times with 4 ml PBS/BSA. Bound radioactivity was determined by liquid scintillation counting in Ecolume cocktail.

Aqueous phase testing of IgG immobilized on nylon rods showed less specific signal and higher background signal than did glass rods used under the same conditions, and therefore, were not selected for further evaluation.

In general, the activity of the immobilized IgG fractions paralleled the activity of the raw sera. Thus, in PBS, two lots of anti-estradiol (NEIA lot #554-C and 462-C) were shown to have high tracer binding capacity, while anti-digitoxin antibodies (Wein lot #04737) and anti-progesterone antibodies (NEIA lot #262-C) were found to be less active.

EXAMPLE 2

Organic Phase Antigen-binding Assays

General procedure

Except as otherwise noted, antigen binding assays were performed according to the following protocol. Either 10 mg of CPG beads or one glass rod or one glass bead with immobilized antibody was added to each 7 ml glass scintillation vial. Each sample then received 1 ml of the specified solvent and 10 µl (0.1 µCi) of [$^3$H]-tracer, dissolved in toluene. Samples were incubated at the specified temperature for the indicated time and then washed three times with 2 ml incubation solvent. Bound radioactivity was determined in 3 ml of Ecolume liquid scintillation cocktail. The aqueous phase binding capacity of immobilized IgG was determined concurrently with all organic phase experiments. Methods for these aqueous phase determinations were identical to those for solvent, except PBS or PBS/BSA was substituted for organic solvent incubation media, and tritiated tracers were diluted in PBS instead of toluene. Statistical analysis was performed on a MacIntosh computer using the Statview statistics program.

Initial screening

Preliminary organic phase experiments utilizing rabbit IgG fractions immobilized on CPG were performed in octane containing 1M propanol and 0.1% PBS (OPP). Tritiated tracer was bound by immobilized anti-estradiol more than to BSA background controls in a preliminary experiment (see Table 1, Exp. 1).

Effect of increasing amounts of AOT on antigen binding

A 50 mM (AOT) in hexane solution was prepared. Dilutions were prepared from this stock solution with anhydrous hexane to give final AOT concentrations of 10 mM, 2mM, 0.2mM, and 0.02 mM. Anti-estradiol and anti-digitoxin were tested at each concentration. One milliliter of hexane containing specified amounts of AOT was added to each sample, followed by 10 µl of [$^3$H]-tracer (0.1 µCi/sample) in anhydrous toluene (Table 2).

It is noteworthy that the background binding of digitoxin tracer was substantially reduced in the presence of AOT. More than 20,000 cpm were bound by anti-digitoxin IgG when compared to normal rabbit IgG (NRIgG) background, at 0.02 mM and 0.2 mM AOT. A differential binding of this magnitude after only two hours suggests that significant binding could have been detected with a shorter period of incubation. Based on these results, 0.2 mM AOT was selected for use in future experiments.

The results presented in Tables 2 and 3 suggest that precise optimization of incubation conditions may be necessary with each antigen/solvent/ antibody combination. Antigen binding by antiestradiol IgG was greatly enhanced by an 18 hr., 4° C. incubation, when compared to a 2 hr, room temperature incubation. However, this was not the case for anti-digitoxin IgG. Following the 18 hr, 4° C. incubation, labelled digitoxin tracer was bound to NRIgG background beads and anti-digitoxin IgG comparably. The result presented in Table 2 shows that after a 2 hr, room temperature incubation, substantial amounts of tracer were bound in excess of background. Anti-progesterone IgG preparations did not seem to bind labelled tracer beyond background under any of these conditions.

Effect of time and temperature on antigen binding in hexane/AOT

Using a preferred combination of estradiol, antibody, and solvent, the time course of tracer binding was studied at room temperature and at 4° C. Antigen-binding assays were performed in PBS-saturated hexane containing 0.2 mM AOT. Samples were incubated for specified time periods at 4° C. or at room temperature (22-25° C.), then washed three times with 2 ml of ice cold hexane/AOT at room temperature hexane/AOT followed by measurement of bound label by scintillation counting.

Unlike the previous observations (Table 2), significant binding of labelled tracer was not detected at any time point when the incubation was performed at room temperature. However, clear antibody binding activity was seen when the incubation was performed at 4° C. Equilibrium binding was achieved following 4 to 8 hr of incubation.

Specific inhibition of tracer binding by unlabeled antigen in hexane/AOT

Antigen-binding assays were performed in PBS saturated hexane with 0.2 mM AOT, prepared as described above. Estradiol inhibitor was prepared as a saturated solution in PBS saturated toluene, then diluted to the indicated concentrations in hexane/AOT. Progesterone was dissolved in hexane/AOT. A toluene vehicle control was included as the zero inhibitor sample (final added toluene concentration =0.1% (v/v)). Radiolabelled tracer, [$^3$H]Estradiol (0.1 μCi/sample), was then added in 10 μl of in anhydrous toluene.

Table 1 indicates the results.

TABLE 1

Antigen-binding assay of anti-estradiol IgG in octane containing 1 M propanol and 0.1% PBS

| Experiment | Immobilized protein | Support | Estradiol inhibitor | cpm bound ± standard error |
|---|---|---|---|---|
| 1[a] | Anti-estradiol | CPG | — | 15409 ± 1030 (n = 5) p ≤ 0.0005) |
| 3[b] | BSA | CPG | — | 9710 ± 235 |
|  | Anti-estradiol | glass rod | — | 181 ± 20 (n = 6) 0.01 < p ≤ 0.025) |
|  | NRIgG | glass rod | — | 85 ± 29 (n = 3) |

[a] Samples incubated in 0.5 ml OPP for 18 hr at 4° C. 1 0μ Ci [$^3$H]estradiol in OPP washed 6× with OPP
[b] Samples incubated in 0.6 ml OPP for 18 hr at 4° C. 1.0μ Ci [$^3$H]estradiol in OPP, washed 3× with OPP
[c] NEIA lot #554-C = anti-estradiol
PBS = 0.01 M Sodium phosphate, 0.15 M NaCl (pH 7.0)
cpm = counts per minute
BSA = bovine serum albumen
OPP = octane containing 1 M 1-propanol and 1% PBS (v/v)
NRIgG = normal rabbit IgG
PBS = 0.01 m Sodium phosphate, 0.15 M NaCl (pH 7.0)
cpm = counts per minute BSA = bovine serum albumen OPP = octane containing 1 M 1-propanol and 1% PBS(v/v) NRIgG = normal rabbit IgG--.

TABLE 2

Effect of increasing amounts of AOT on antigen binding by rabbit IgG
Counts bound (means cpm of duplicate or triplicate determinations)

| Sample | AOT concentration | | | | | |
|---|---|---|---|---|---|---|
|  | 0 | 0.02 mM | 0.2 mM | 2 mM | 10 mM | 50 mM |
| NRIgG-E* | 6351 | 1639 | 379 | 553 | 409 | 509 |
| Anti-Est. 554-C | 7887 | 1173 | 648 | 737 | 543 | 585 |
| NRIgG-D* | 60230 | 30444 | 29155 | 29828 | N.D. | N.D. |
| Anti-Dig 04737 | 62231 | 54363 | 53506 | 43133 | N.D. | N.D. |

Samples were incubated 2 hours at room temperature
E* = [$^3$H]Estradiol background
D* = [$^3$H]Digitoxin background
AOT = dioctyl sulfosuccinate sodium salt
cpm = counts per minute
NRIgG-E* = normal rabbit IgG-estradiol
Anti-Est. 554-C = anti-estradiol (non-specific binding control)
NRIgG-D* = normal rabbit IgG-digitoxin
Anti-Dig 04737 = anti-digitoxin
ND = not determined --AOT=dioctyl sulfosuccinate sodium salt cpm=counts per minute NRIgG-E*=normal rabbit IgG-estradiol Anti-Est. 554-C=anit-estradiol (non-specific binding control) NRIgG-D*=normal rabbit IgG-digitoxin Anti-Dig. 04737=anti-digitoxin ND=not determined--.

TABLE 3

Antigen binding assay of anti-estradiol, anti-progesterone and anti-digitoxin IgG in PBS saturated solvents containing 0.2 mM AOT (Mean cpm of duplicate determinations)

| Solvent | NRIgG-E*[1] | Anti-Estradiol 554-C | Anti-Estradiol 462-C | NRIgG-P*[1] | Anti-Progesterone 262-C | NRIgG-D*[1] | Anti-Digitoxin 04737 |
|---|---|---|---|---|---|---|---|
| PBS/BSA | 80 | 3777 | 2874 | 44 | 226 | 105 | 402 |
| Acetonitrile[2] | 223 | 267 | 395 | 53 | 345 | 470 | 604 |
| Toluene | 306 | 827 | 561 | 290 | 157 | 784 | 1224 |
| Butyl Ether | 260 | 324 | 277 | 205 | 332 | 2517 | 1337 |
| Hexane | 900 | 7905 | 2355 | 462 | 505 | 44233 | 46399 |
| Octane | 745 | 6392 | 3711 | 223 | 249 | 60999 | 68376 |

[1] E* = [$^3$H]Estradiol background, D* = [$^3$H]Digitoxin background, P* = [$^3$H]Progesterone background
[2] 0.1% PBS (v/v) added
Samples incubated for 18 hr at 4° C
PBS/BSA = 0.01 M Sodium phosphate, 0.15 M NaCl (pH 7.0) with 1% bovine serum albumin
cpm = counts per minute
NRIgG-E* = Normal rabbit IgG-estradiol non-specific binding control
Anti-Estradiol 554-C = anti-estradiol lot
Anti-Estradiol 462-C =
NRIgG-P* = normal rabbit IgG-progesterone
Anti-Progesterone 262-C = anti-progesterone lot
NRIgG-D* = Normal rabbit IgG-digitoxin
Anti-Digitoxin 04737 = anti-digitoxin lot
AOT = dioctyl sulfosuccinate sodium salt --PBS/BSA=0.01 M sodium phosphate, 0.15 M NaCl (pH 7.0) with 1% bovine serum albumin cpm=counts per minute NRIgG-E*=Normal rabbit IgG-estradiol non-specific binding control Anti-Estradiol 554-C=anti-estradiol lot Anti-Estradiol 464-C=NRIgG-P*=normal rabbit IgG-progesterone Anti-Progesterone 262-C=anti-progesterone lot NRIgG-D*=Normal rabbit IgG-digitoxin Anti-Digitoxin 04737=anti-digitoxin lot AOT=dioctyl sulfosuccinate sodium salt--.

TABLE 4

Organic Phase Radioimmunoassay for Estradiol
Counts [$^3$H] Estradiol Bound (mean ± S.D., n = 9)

| Sample | ng/ml Estradiol Inhibitor | | | | | |
|---|---|---|---|---|---|---|
|  | 0 | 200 | 20 | 2 | 0.2 | 1 μg prog. |
| NRIgG | 595 ± 163 | 499 ± 107 | 513 ± 121 | 485 ± 91 | 510 ± 103 | 500 ± 75 |
| #554-C | 3639 ± 1016 | 545 ± 124 | 592 ± 120 | 1137 ± 302 | 2618 ± 642 | 3189 ± 1142 |

TABLE 4-continued

Organic Phase Radioimmunoassay for Estradiol
Counts [³H] Estradiol Bound (mean ± S.D., n = 9)

| Sample | ng/ml Estradiol Inhibitor | | | | | 1 μg prog. |
|---|---|---|---|---|---|---|
| | 0 | 200 | 20 | 2 | 0.2 | |
| #462-C | 1789 ± 501 | 499 ± 106 | 514 ± 130 | 662 ± 93 | 1299 ± 273 | 1779 ± 554 |

18 hr incubation at 4° C in hexane 0.2 mM AOT
S.D. = Standard Deviation
NRIgG = normal rabbit IgG
554-C = anti-estradiol lot
462-C = anti-estradiol lot
AOT = dioctyl sulfosuccinate sodium salt
prog. = progesterone --S.D.=Standard Deviation NRIgG=normal rabbit IgG #554-C=anti-estradiol #462-C=anti-estradiol AOT=dioctyl sulfosuccinate sodium salt prog.=progesterone--.

The antigen binding activity of antiestradiol was significantly greater than for NRIgG ($p<0.0005$). A detection limit of 200 pg/ml was achieved with both lots of anti-estradiol (lot #554-C, $0.01<p \leq 0.025$; lot #462-C, $0.005 <p \leq 0.01$). Specificity of the reaction was demonstrated by the lack of cross-reaction with 1 μg/ml of progesterone (lot #554-C, $0.1 <p \leq 0.375$; lot 462-C, $p >0.4$).

EXAMPLE 3

Comparison of Solvents for Organic Phase RIA

Duplicate samples of rabbit antiestradiol IgG (lot 554-C, New England Immunology Associates) covalently immobilized on 3 mm Pyrex ™ 0 glass beads (Aldrich) were incubated in 1 ml of the specified medium for 18 h. at 4° C. with increasing amounts of [³H]Estradiol (Amersham, specific activity 110.5 Ci/mmol). Duplicate samples of antigen nonspecific rabbit IgG (Pierce) similarly immobilized were incubated in parallel, and served as controls for non-specific binding of [³H]Estradiol. A 0.1 ml sample of the supernatant, containing free, unbound [³H]Estradiol, was taken prior to washing of the solid phase. Following incubation, the solid-phase antibodies were washed three times with 2 ml of 4° C. incubation medium. All solvents were of anhydrous grade (Aldrich). Bound and free [³H]Estradiol was counted using standard liquid scintillation counting techniques. Scatchard analysis of the data was performed using the "EBDA" and "LIGAND" programs (Biosoft) on a 2.5 megabyte RAM Macintosh SE computer (Apple).

Determination of Solvent Water Content

Solvent water content was determined by Karl Fischer titrations performed by the dead-stop technique, using an Aquametry II apparatus (Lab Industries). Stabilized pyridine-free Karl Fischer reagent (KFR) was purchased from GFS Chemical (Powell, Ill.). Our limit of detection was determined by the minimum buret reading (0.05 ml), the concentration of KFR and the sample aliquot (2 ml). The commercial KFR had a titer of 6.16 mg H₂O/ml KFR. This was diluted to a titer of 1.61 mg H₂O/ml KFR. Further dilutions gave irreproducible titration results. The limit of detection was 0.08 mg H₂O (approximately 0.002% (w/w) depending on the density of the solvent). A solution comprised of 15% methanol in methylene chloride (v/v) served as diluent. The water equivalence titer, F, of the KFR was determined prior to each experimental session (F =mg H₂O/ml KFR). The titration endpoint was established by the use of a conductivity meter.

Weighed samples containing unknown amounts of water were added to the reaction vessel and titrated to the endpoint with KFR. Water content of the samples was calculated with the following formula:

$$\% H_2O (w/w) = \frac{ml\ KFR \times F \times 0.1}{wt.\ of\ sample\ (grams)}$$

Scatchard Analysis of Antigen — Antibody Binding in Water Immiscible Solvents According to Rodbard (in Ligand Assays Langan and Clapp (eds) Massan Publishing, N.Y. pp 45–101), the Scatchard plot is one of the most useful methods for the analysis of antigen-antibody binding. When an equilibrium between antigen and antibody is reached, there is a linear relationship between the bound to free ratio for the ligand and the concentration of bound ligand. The slope of this line is $-1$ times the affinity constant ), the intercept on the horizontal axis is the concentration of binding sites present ($B_{max}$), and the intercept on the vertical axis is ($K_{aff} \times B_{max}$). In systems containing a single homogeneous ligand which reacts with multiple classes of receptor, a nonlinear or "concave" Scatchard plot may be observed. Such is often the case with polyclonal antibodies since they contain multiple populations of antibodies which may vary both in their frequency and equilibrium constant. Equilibrium-binding data of heterogenous receptor (e.g. antibody) systems may be evaluated with mathematical models which assume the presence of a single receptor site, two receptor sites, and so on. We have performed Scatchard analysis of antigen-antibody binding in aqueous medium and in a series of nearly anhydrous organic solvents using one- and two-site models for this interaction. While neither of these models is expected to provide an exact measurement of the $K_{aff}$ and $B_{max}$, since a polyclonal IgG represents a heterogeneous receptor population, reasonably accurate values for these parameters can be estimated.

The data presented in Tables 5 and 6 illustrate that specific high affinity antigen-antibody interaction does occur in nearly anhydrous organic media. In all cases, a one-site Scatchard plot model could be applied to the data (Table 5). In several experiments, the data could also be interpreted with a two-site Scatchard plot model (Table 6).

In the "conventional" system, where the antibody-antigen binding takes place in aqueous PBS-T, the data were best expressed by a one-site model. The equilibrium constant obtained ($2.33 \times 10^9 \pm 0.24 \times 10^9 M^{-1}$) can be compared to the systems employing nearly anhydrous organic media, organic media saturated with PBS, pH 7, and organic media saturated with PBS and supplemented with 0.2 mM AOT. In all cases, the water content of the organic media was less than 0.1% (w/w), as determined by the Karl Fischer titration (Table 7). The method is described above.

In hexane, the affinity constant derived from the one-site model was comparable to that obtained in the aqueous system. However, when a 2site model was applied to the data, a fraction of the total antibody could be detected which had an increased affinity constant, when compared to that obtained in the aqueous system. It was not necessary to saturate hexane with PBS, or to add surfactant to the system in order to observe this effect. However, the addition of surfactant did lower non-specific binding of [$^3$H]Estradiol to antigen non-specific IgG controls, thus serving to enhance the "signal to noise" ratio of the system. This surprising result suggests that certain antibodies can be selected which will function well under nearly anhydrous conditions. Antibodies which exhibit high affinity in organic media might be exploited to produce more sensitive immunoassay procedures, rapid immunoaffinity separations, and catalytic antibodies for use with lipophilic analytes such as estradiol or those analytes having intermediate solubility in hydro-phobic solvents, such as digitoxin.

Significant binding with the estradiol/anti-estradiol system was also observed in nearly anhydrous toluene and carbon tetrachloride In these solvents there was a modest reduction in the apparent affinity constants, when interpreted with one-site Scatchard models. However, in those cases where a two-site Scatchard model could be employed, populations of antibodies with affinity comparable to the aqueous system were detected. This observation suggests that antibodies can be selected which will function in water immiscible aliphatic, alicyclic and aromatic hydrocarbous, and chlorinated solvents, with binding activity comparable to that obtained in aqueous media.

TABLE 5

Scatchard Analyses of Equilibrium Saturation Binding of [$^3$H]Estradiol to Anti-Estradiol IgG at 4° C.

| Solvent | PBS sat | 0.2 mM AOT | One-site Scatchard Model ($K_{aff} \pm$ S.E.) $M^{-1}$ | One-site Scatchard Model ($B_{max} \pm$ S.E.) Mol/liter | Number of duplicate data points (n) |
|---|---|---|---|---|---|
| Hexane | no | no | $5.12 \cdot 10^9 \pm 1.20 \cdot 10^9$ | $8.02 \cdot 10^{-11} \pm 0.67 \cdot 10^{-11}$ | 15 |
| Hexane | yes | no | $2.59 \cdot 10^9 \pm 0.84 \cdot 10^9$ | $8.08 \cdot 10^{-11} \pm 1.12 \cdot 10^{-11}$ | 14 |
| Hexane | yes | yes | $5.91 \cdot 10^9 \pm 1.19 \cdot 10^9$ | $8.70 \cdot 10^{-11} \pm 0.65 \cdot 10^{-11}$ | 13 |
| Toluene | no | no | $2.37 \cdot 10^8 \pm 0.55 \cdot 10^8$ | $1.86 \cdot 10^{-11} \pm 0.35 \cdot 10^{-11}$ | 15 |
| Toluene | yes | no | $3.51 \cdot 10^8 \pm 0.61 \cdot 10^8$ | $3.24 \cdot 10^{-11} \pm 0.42 \cdot 10^{-11}$ | 15 |
| Toluene | yes | yes | $2.89 \cdot 10^8 \pm 0.42 \cdot 10^8$ | $2.93 \cdot 10^{-11} \pm 0.33 \cdot 10^{-11}$ | 15 |
| Carbon Tetrachloride | no | no | $3.94 \cdot 10^8 \pm 0.54 \cdot 10^8$ | $9.06 \cdot 10^{-12} \pm 0.85 \cdot 10^{-12}$ | 4 |
| Carbon Tetrachloride | yes | no | $8.04 \cdot 10^8 \pm 0.74 \cdot 10^8$ | $2.29 \cdot 10^{-11} \pm 0.14 \cdot 10^{-11}$ | 5 |
| Carbon Tetrachloride | yes | yes | $1.08 \cdot 10^9 \pm 0.38 \cdot 10^9$ | $1.92 \cdot 10^{-11} \pm 0.42 \cdot 10^{-11}$ | 5 |
| Phosphate Buffered Saline + 0.05% Tween-20 | — | no | $2.33 \cdot 10^9 \pm 0.24 \cdot 10^9$ | $9.83 \cdot 10^{-11} \pm 0.60 \cdot 10^{-11}$ | 10 |

S.E. = Standard Error
PBS sat = organic media saturated with 0.01 M sodium phosphate, 0.15 M NaCl (pH 7.0)
AOT = dioctyl sulfosuccinate sodium salt
Tween 20 = surfactant

TABLE 6

Scatchard Analyses of Equilibrium Saturation Binding of [$^3$H]Estradiol to Anti-Estradiol IgG at 4° C.

| Solvent | PBS sat | 0.2 mM AOT | Two-site Scatchard Model ($K_{aff} \pm$ S.E.) High affinity population $M^{-1}$ | Two-site Scatchard Model ($B_{max} \pm$ S.E.) High affinity population Mol/liter | Two-site Scatchard Model ($K_{aff} \pm$ S.E.) Low affinity polulation $M^{-1}$ | Two-site Scatchard ($B_{max} \pm$ S.E.) Low affinity population Mol/liter | Number of duplicate data points (n) |
|---|---|---|---|---|---|---|---|
| Hexane | no | no | $2.62 \cdot 10^{10} \pm 3.44 \cdot 10^{10}$ | $3.48 \cdot 10^{-11} \pm 1.86 \cdot 10^{-11}$ | $6.47 \cdot 10^8 \pm 7.00 \cdot 10^8$ | $7.13 \cdot 10^{-11} \pm 1.60 \cdot 10^{-11}$ | 15 |
| Hexane | yes | no | $1.03 \cdot 10^{10} \pm 1.42 \cdot 10^{11}$ | $4.04 \cdot 10^{-11} \pm 2.45 \cdot 10^{-11}$ | $7.52 \cdot 10^7 \pm 3.98 \cdot 10^8$ | $1.63 \cdot 10^{-10} \pm 1.60 \cdot 10^{-10}$ | 14 |
| Hexane | yes | yes | $9.69 \cdot 10^9 \pm 4.87 \cdot 10^9$ | $6.61 \cdot 10^{-11} \pm 1.88 \cdot 10^{-11}$ | $1.16 \cdot 10^8 \pm 4.66 \cdot 10^8$ | $7.09 \cdot 10^{-11} \pm 1.31 \cdot 10^{-10}$ | 13 |
| Toluene | no | no | Not determined | Not determined | Not determined | Not determined | 15 |
| Toluene | yes | yes | $1.22 \cdot 10^9 \pm 1.59 \cdot 10^9$ | $5.10 \cdot 10^{-12} \pm 2.10 \cdot 10^{-11}$ | $1.46 \cdot 10^8 \pm 2.74 \cdot 10^9$ | $3.89 \cdot 10^{-11} \pm 1.07 \cdot 10^{-9}$ | 15 |
| Toluene | yes | yes | Not determined | Not determined | Not determined | Not determined | 15 |
| Carbon Tetra-Chloride | no | no | Not determined | Not determined | Not determined | Not determined | 4 |
| Carbon Tetra-Chloride | yes | no | Not determined | Not determined | Not determined | Not determined | 5 |
| Carbon Tetra-Chloride Phospate Buffered Saline + 0.05% | yes | yes | $6.94 \cdot 10^9 \pm 1.27 \cdot 10^9$ | $4.23 \cdot 10^{-12} \pm 0.56 \cdot 10^{-12}$ | $1.14 \cdot 10^8 \pm 0.32 \cdot 10^8$ | $3.98 \cdot 10^{-11} \pm 0.61 \cdot 10^{-11}$ | 5 |

TABLE 6-continued

| Solvent | PBS sat | 0.2 mM AOT | Two-site Scatchard Model ($K_{aff}$ ± S.E.) High affinity population $M^{-1}$ | Two-site Scatchard Model ($B_{max}$ ± S.E.) High affinity population Mol/liter | Two-site Scatchard Model ($K_{aff}$ ± S.E.) Low affinity polulation $M^{-1}$ | Two-site Scatchard ($B_{max}$ ± S.E.) Low affinity population Mol/liter | Number of duplicate data points (n) |
|---|---|---|---|---|---|---|---|
| Tween-20 | — | no | Not determined | Not determined | Not determined | Not determined | 10 |

Scatchard Analyses of Equilibrium Saturation Binding of [³H]Estradiol to Anti-Estradiol IgG at 4° C S.E. = Standard Error
PBS sat = organic media saturated with 0.01 M sodium phosphate, 0.15 M NaCl (pH 7.0)
Tween-20 = surfactant
AOT = dioctyl sulfosuccinate sodium salt --S.E. = Standard Error PBS sat. = organic media saturated with 0.01 M sodium phosphate, 0.15 M NaCl (pH 7.0) Tween-20 = surfactant AOT = dioctyl sulfosuccinate sodium salt--.

TABLE 7

Water content of solvent systems employed in organic phase immunochemistry experiments

| Trial | Sample | Anhydrous | PBS Saturated | PBS Saturated with 0.2 mM AOT |
|---|---|---|---|---|
| | | [% H₂O (w/w mean ± standard deviation)] | | |
| 1 | Hexane | 0.0038 ± 0.0002 | 0.0152 | N.D. |
| 2 | Hexane | N.D. | 0.0118 ± 0.002 | 0.008 |
| 3 | Hexane | 0.0093 ± 0.0002 | 0.0133 ± 0.0018 | 0.0110 ± 0.0020 |
| 1 | Toluene | 0.0049 | 0.0605 ± 0.004 | 0.0515 ± 0.0029 |
| 2 | Toluene | 0.0105 ± 0.0013 | 0.0663 | 0.0622 ± 0.0008 |
| 3 | Toluene | 0.0094 ± 0.0004 | 0.0507 ± 0.0041 | 0.0478 ± 0.0023 |
| 4 | Toluene | 0.0095 ± 0.0004 | 0.0721 ± 0.0017 | 0.0478 ± 0.0023 |
| 1 | Carbon Tetrachloride | 0.0080 ± 0.0004 | 0.0133 ± 0.0013 | 0.0130 ± 0.0005 |
| 2 | Carbon Tetrachloride | 0.0069 ± 0.0006 | 0.0116 ± 0.0013 | 0.0144 ± 0.0005 |
| 3 | Carbon Tetrachloride | 0.0081 ± 0.0004 | 0.0113 ± 0.0001 | 0.0107 ± 0.0004 |

PBS sat = organic media saturated with 0.01 M sodium phosphate, 0.15 M NaCl (pH 7.0)
AOT = dioctyl sulfosuccinate sodium salt --PBS sat. = organic media saturated with 0.01 M sodium phosphate, 0.15 M NaCl (pH 7.0) AOT = dioctyl sulfosuccinate sodium salt--.

It is evident from the above results, that accurate assays may be carried out with a wide variety of analytes in hydrophobic media. Therefore, the subject methodology offers many advantages in those situations where an aqueous medium is undesirable or not available. The subject invention finds particular application with hydrophobic or lipophilic analytes, in systems involving organic solvent media, and the like.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for detecting the presence of a lipophilic ligand analyte in a sample employing a proteinaceous receptor which is an antibody or a binding fragment thereof, wherein said lipophilic ligand analyte and said receptor are members of a specific antigen-antibody binding pair, said method comprising:

combining to form an assay medium a solvent system comprising a solvent characterized as hydrophobic, essentially anhydrous and water immiscible and comprising an aliphatic or aromatic hydrocarbon or a halohydrocarbon, (2) a reagent system for providing a detectable signal, wherein said reagent system comprises (i) a labelled ligand conjugate and (ii) said proteinaceous receptor, and (iii) any additional reagents for detecting complex formation between said labelled ligand conjugate and said receptor, and (3) said lipophilic ligand analyte in either (i) an amount and composition of aqueous medium capable of dispersion in said solvent system or (ii) a solvent substantially miscible with said solvent system;

removing any unbound labelled conjugate, with the proviso that said assay medium may be separated from any complexes which are formed prior to addition of any remaining members of said reagent system; and detecting the presence of said signal, where a decrease in the amount of signal detected in said sample as compared to a control containing no analyte is indicative of the presence of said analyte.

2. The method according to claim 1, wherein said solvent system further comprises:

at least one of not more than about 5% (w/w) of an aqueous buffered solution at a pH in the range of about 5 to 10 and from zero up to about 5 mM of a anionic surfactant.

3. The method according to claim 2, wherein said solvent is an aliphatic or aromatic hydrocarbon or halohydrocarbon and said solvent is saturated with said aqueous buffered solution.

4. The method according to claim 1, wherein said receptor is bound to a solid support.

5. A method for detecting the presence of a lipophilic ligand analyte in a sample employing a proteinaceous receptor which is an antibody or a binding fragment thereof bound to a solid support, wherein said lipophilic ligand analyte and said receptor are members of a specific antigen-antibody binding pair, said method comprising:

combining to form an assay medium (1) a solvent system comprising a solvent characterized as hydrophobic, essentially anhydrous and water immiscible, where said solvent is an aromatic hydrocarbon, an aliphatic hydrocarbon or a halohydrocarbon, not more than about 5% (w/w) of an aqueous buffered solution at a pH in the range of about 5 to 10, and from zero up to about 5 mM of an anionic surfactant, and a (2) reagent system for providing a detectable signal, where said reagent system comprises a labelled ligand conjugate and said receptor, and (3) said lipophilic ligand analyte in either (i) an amount and composition of aqueous medium capable of dispersion in said solvent system or (ii) a solvent substantially miscible with said solvent system;

separating said assay medium from any complexes which have formed;

adding any additional reagents for detecting complex formation between said labelled ligand conjugate and said receptor to said support or said assay medium; and detecting the presence of said signal, where a decrease in the amount of signal detected in said sample as compared to a control containing no analyte is indicative of the presence of said analyte.

6. The method according to claim 5, wherein said aliphatic hydrocarbon is a straight chain hydrocarbon of from 6 to 16 carbon atoms and said detergent is a sulfo salt.

7. The method according to claim 1 or claim 5, wherein said labelled of said labeled conjugate is a radioisotope, a fluorescer or a chemiluminescer.

8. The method according to claim 2 or claim 5, wherein said aqueous buffered solution is present in not more than about 2% (w/w) and said surfactant is an anionic surfactant present at from about 0.01 to 1 mM.

9. The method according to claim 5, wherein said solid support comprises activated glass beads.

10. The method according to claim 9, wherein prior to addition to said combining, said proteinaceous receptor bound to a solid support is lyophilized.

11. The method according to claim 1 or claim 5, wherein said solvent comprises hexane, carbon tetrachloride or toluene.

12. A kit for use in the detection of a lipophilic analyte by immunoassay, said kit comprising:

in a first container (a) a solvent system comprising (i) a solvent characterized as hydrophobic, essentially anhydrous and water immiscible, wherein said solvent comprises an aromatic hydrocarbon, an aliphatic hydrocarbon or a halohydrocarbon, not more than about 5% (w/w) of an aqueous buffered solution at a pH in the range of about 5 to 10, and (ii) from zero up to about 5 mM of an anionic surfactant for inhibiting non-specific binding; (b) a reagent system comprising a labelled ligand conjugate is cross-reactive with said anti-analyte antibody or binding fragment thereof, wherein said labelled ligand conjugate is cross-reactive with said analyte, and in a second container, any additional reagents for detecting complex formation between said labelled ligand conjugate and said antibody.

13. A kit for detection of a lipophilic analyte by immunoassay, said kit comprising:

in a first container (a) a solvent system comprising (i) a solvent characterized as hydrophobic, essentially anhydrous and water immiscible, wherein said solvent comprises an aromatic hydrocarbon, an aliphtic hydrocarbon or a halohydrocarbon, not more than about 5% (w/) of an aqueous buffered solution at a pH in the range of about 5 to 10, and (ii) from zero up to about 5 mM of an anionic surfactant for inhibiting non-specific binding; and (b) an anti-analyte antibody or binding fragment thereof; in a second container, a reagent system comprising a labelled ligand conjugate, wherein said labelled ligand conjugate is cross-reactive with said analyte; and in a third container, any additional reagents for detecting complex formation between said labelled conjugate and said antibody.

14. A kit for detection of a lipophilic analyte by immunoassay, said kit comprising:

in a first container (a) a solvent system comprising (i) a solvent characterized as hydrophobic, essentially anhydrous and water immiscible, wherein said solvent comprises an aromatic hydrocarbon, an aliphatic hydrocarbon or a halohydrocarbon, not more than about 5% (w/w) of an aqueous buffered solution at a pH in the range of abut 5 to 10, and (ii) from zero up to about 5 mM of an anionic surfactant for inhibiting non-specific binding; in a second container, a reagent system comprising a labelled ligand conjugate, wherein said labelled ligand conjugate is cross-reactive with said analyte; in a third container, an anti-analyte antibody or binding fragment thereof; and in a fourth container, any additional reagents for detecting complex formation between said labelled conjugate and said antibody.

15. The kit according to any one of claim 12—14, further comprising in an additional container, a solid support for use in said immunoassay.

16. The kit according to any one of claim 12—14, wherein said anti-analyte antibody or binding fragment thereof is bound to a solid support.

17. The kit according to any one of claim 12—14, wherein said anti-analyte antibody or binding fragment thereof is bound to a solid support and lyophilized.

18. The kit according to any one of claim 12—14, wherein said anti-analyte antibody is bound to a solid support comprising glass beads.

19. The kit according to claim 12, wherein said anti-analyte antibody is lyophilized anti-analyte antibody bound to a solid support comprising glass beads.

20. The kit according to any one of claim 12—14, wherein said solvent comprises hexane, carbon tetrachloride or toluene.

21. In a method for detecting a lipophilic ligand analyte by detecting decreased labelled analyte-antianalyte binding as compared to a control containing no analyte by immunoasay which comprises combining a sample containing an analyte with an anti-ligand antibody or binding fragment thereof and a labelled ligand conjugate, wherein said ipophilic ligand analyte and said anti-ligand are members of a specific antigen-antibody pair and aid labelled ligand conjugate is cross-reactive with said lipophilic ligand analyte, whereby the binding of antiligant antibody and labelled ligand conjugate results in a detectable signal and determining said detectable signal, the improvement which comprises:

the use as a reaction medium for said immunoassay of a solvent system comprising (i) a solvent characterized as hydrophobic, essentially anhydrous and water immiscible, wherein said solvent comprises an aromatic hydrocarbon, an aliphatic hydrocarbon or a halohydrocarbon, not more than about 5% (w/w) of an aqueous buffered solution at a pH in the range of about 5 to 10, and (ii) from zero up to about 5 mM of an anionic surfactant for inhibiting non-specific binding.

22. The method according to claim 21, wherein said solvent comprises hexane, carbon tetrachloride or toluene.

* * * * *

UNITED STATES PATENT AND TRADEMARK OFFICE
CERTIFICATE OF CORRECTION

PATENT NO. : 5,118,607

DATED : June 2, 1992

INVENTOR(S) : Gary S. Bignami, et al

It is certified that error appears in the above-indentified patent and that said Letters Patent is hereby corrected as shown below:

Column 2, line 51, "or signal to noise ratio," should be --(or signal to noise ratio,)--. Column 4, line 60, "F(ab)2" should be --F(ab')2--; "Fab,," should be --Fab',--. Column 6, line 67, "Ci/mmol" should be further indented to indicate it is a continuation of the text on line 66. Column 7, line 18, "Sepharose=4B" should be --Sepharose™ 4B--; line 52, "0.1μCi" should be --0.1 μCi--; line 53, "0.1M" should be --0.1 M--; line 65, "0.1N" should be --0.1 N--. Column 8, lines 6, 7, 54, 56, and 58 "Pyrex TM", each occurrence should be --Pyrex™--; line 28, "Biochem." should be --Biochim.--; line 66, "Drierite TM" should be --Drierite™--. Column 9, line 6, "titratio" should be --titration--. Column 10, line 9, "T itiated" should be --Tritiated--; line 15, "(AOT)" should be --AOT--; line 59, "at" should be --or with--. Column 11, line 14, "Table 1" should be --Table 4--. Column 11, line 58 through column 12, line 2 delete "PBS=0.01m Sodium phosphate, 0.15 M NaCl (pH 7.0) cpm=counts per minute BSA=bovine serum albumen OPP=octane containing 1 M 1-propanol and 1% PBS(v/v) NRIgG=normal rabbit IgG--.". Table 3, after Anti-Estradiol 462-C= insert--anti-estradiol lot--. Column 12, lines 23 through 28 delete "--AOT=dioctyl sulfosuccinate sodium salt cpm=counts per minute NRIgG-E*=normal rabbit IgG-estradiol Anti-Est. 554-C=anit-estradiol (non-specific binding control) NRIgGD*=normal rabbit IgG-digitoxin Anti-Dig. 04737=anti-digitoxin ND=not determined--.".

UNITED STATES PATENT AND TRADEMARK OFFICE
CERTIFICATE OF CORRECTION

PATENT NO. : 5,118,607
DATED : June 2, 1992
INVENTOR(S) : Gary S. Bignami, et al It is certified that error appears in the above-indentified patent and that said Letters Patent is hereby corrected as shown below:

Column 12, lines 52 through 60 delete "--PBS/BSA=0.01 M sodium phosphate, 0.15 M NaCl (pH 7.0) with 1% bovine serum albumin cpm=counts per minute NRIgG-E*=Normal rabbit IgG-estradiol non-specific binding control Anti-Estradiol 554-C=an-ti-estradiol lot Anti-Estradiol 464-C=NRIgG-P*=nor-mal rabbit IgG-progesterone Anti-Progesterone 262-C=anti-progesterone lot NRIgG-D*=Normal rabbit IgG-digitoxin Anti-Digitoxin 04737=anti-digitoxin lot AOT=dioctyl sulfosuccinate sodium salt--.". Column 13, lines 13 through 17 delete "--S.D.=Standard Deviation NRIgG=normal rabbit IgG #554-C=anti estradiol #462-C=anti-estradiol AOT=dioctyl sulfosuccinate sodium salt prog.=progestrone--."; line 31, "Pyrex TM0" should be --Pyrex™--. Column 14, line 31, remove the return after line; line 32, ")" should be --$(K_{aff})$--. Column 15, line 5, "2site" should be --2-site--. Column 16, line 1, "analates such as estradiol" should be --analates, such as estradiol,--; line 2, "hydro-phobic" should be --hydrophobic--; lines 40 through 43 delete "--S.E.=Standard Error PBS sat.=organic media saturated with 0.01 M sodium phosphate, 0.15 M NaCl (pH 7.0) AOT=dioctyl sulfosuccinate sodium salt Tween 20=surfactant--.".

UNITED STATES PATENT AND TRADEMARK OFFICE
CERTIFICATE OF CORRECTION

PATENT NO. : 5,118,607
DATED : June 2, 1992
INVENTOR(S) : Gary S. Bignami, et al It is certified that error appears in the above-indentified patent and that said Letters Patent is hereby corrected as shown below:

Column 17, lines 10 through 13 delete "--S.E.=Standard Error PBS sat.=organic media saturated with 0.15 M NaCl (pH 7.0) Tween-20=surfactant AOT=dioctyl sulfosuccinate sodium salt--."; lines 42 through 44 delete "--PBS sat.=organic media saturated with 0.01 M sodium phosphate, 0.15 M NaCl (pH 7.0) AOT=diocytl sulfosuccinate sodium salt--.".
In claim 7, column 19, line 21 "wherein said labelled of said labeled" should be -- wherein said label of said labelled --.

Signed and Sealed this

Fourteenth Day of December, 1993

Attest:

BRUCE LEHMAN

*Attesting Officer*  *Commissioner of Patents and Trademarks*